(12) United States Patent
Kwon et al.

(10) Patent No.: US 7,588,901 B2
(45) Date of Patent: Sep. 15, 2009

(54) MODULATION OF ANGIOGENESIS THROUGH TARGETING OF ARGINYL TRANSFERASE (ATE1)

(75) Inventors: Yong Tae Kwon, Wexford, PA (US);
Anna Kashina, Boca Raton, FL (US);
Alexander Varshavsky, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 85 days.

(21) Appl. No.: 11/473,568

(22) Filed: Jun. 22, 2006

(65) Prior Publication Data
US 2006/0234313 A1 Oct. 19, 2006

Related U.S. Application Data (62) Division of application No. 10/394,765, filed on Mar. 21, 2003, now abandoned.

(60) Provisional application No. 60/366,207, filed on Mar. 21, 2002, provisional application No. 60/366,218, filed on Mar. 21, 2002.

(51) Int. Cl.
| | |
|---|---|
| G01N 33/53 | (2006.01) |
| G01N 33/573 | (2006.01) |
| G01N 33/533 | (2006.01) |
| G01N 33/535 | (2006.01) |
| C12Q 1/48 | (2006.01) |
| C12Q 1/02 | (2006.01) |
| C12N 9/10 | (2006.01) |
| C12N 15/54 | (2006.01) |
| C12N 15/81 | (2006.01) |
| C12N 11/16 | (2006.01) |

(52) U.S. Cl. .................. 435/7.21; 435/7.71; 435/8; 435/15; 435/69.2; 435/193; 435/252.3; 435/252.33; 435/254.11; 514/1

(58) Field of Classification Search ............. None
See application file for complete search history.

(56) References Cited

U.S. PATENT DOCUMENTS

| | | | |
|---|---|---|---|
| 6,248,327 B1 | 6/2001 | Daniel et al. | |
| 6,979,551 B2 | 12/2005 | Issakani et al. | |
| 7,262,005 B1 * | 8/2007 | Stack et al. | 435/6 |

FOREIGN PATENT DOCUMENTS

| | | | |
|---|---|---|---|
| WO | WO 98/23283 | * | 6/1998 |
| WO | WO 99/13077 | * | 3/1999 |

OTHER PUBLICATIONS

Gonda et al, J Biol Chemistry 264(28): 16700-16712, 1989.*
Kwon, Y.T. et al., "An Essential Role of N-Terminal Arginylation in Cardiovascular Development," *Science*, vol. 297, Jul. 5, 2002, pp. 96-99.
Kwon, Y.T. et al., "Alternative Splicing Results in Differential Expression, Activity, and Localization of the Two Forms of Arginyl-tRNA-Protein Transferase, a Component of the N-End Rule Pathway," *Molecular and Cellular Biology*, vol. 19, No. 1, Jan. 1999, pp. 182-193.
Baker & Varshavsky, "Inhibition of the N-end rule pathway in living cells", *Proc. Natl. Acad. Sci. USA*, 88:1090-1094 (1991).
Davydov & Varshavsky, "RGS4 Is Arginylated and Degraded by the N-end Rule Pathway in Vitro", *The Journal of Biological Chemistry*, 275(30):22931-22941 (2000).
Stryer et al., In Biochemistry, Third Edition, Stanford University, W.H. Freeman & Company, New York, pp. 31-33 (1998).

* cited by examiner

*Primary Examiner*—Phuong Huynh
(74) *Attorney, Agent, or Firm*—DLA Piper LLP (US)

(57) ABSTRACT

The invention provides methods and compositions for modulating angiogenesis in a subject. The methods of modulating angiogenesis in a subject include administering to the subject a modulator of N-terminal arginylation activity. The invention also provides a method of identifying such a modulator and a method of in vitro screening for modulators of N-terminal arginylation activity. Additionally, the invention provides a method of treating an angiogenesis-related disorder.

24 Claims, 6 Drawing Sheets

MAFWAGGSPSVVDYFPSEDFYRCGYCKNESGSRSNGMWAHSMTVQDYQDLID
RGWRRSGKYVYKPVMNQTCCPQYTIRCRPLQFQPSKSHKKVLKKMLKFLAKGE
VPKGSCEDEPMDSTMDDAVAGDFALINKLDIQCDLKTLSDDIKESLESEGKNSKK
EEPQELLQSQDFVGEKLGSGEPSHSVKVHTVPKPGKGADLSKPPCRKAKEIRKER
KRLKLMQQNPAGELEGFQAQGHPPSLFPPKAKSNQPKSLEDLIFESLPENASHKL
EVRVVRSSPPSSQFKATLLESYQVYKRYQMVIHKNPPDTPTESQFTRFLCSSPLEA
ETPPNGPDCGYGSFHQQYWLDGKIIAVGVIDILPNCVSSVYLYYDPDYSFLSLGV
YSALREIAFTRQLHEKTSQLSYYYMGFYIHSCPKMKYKGQYRPSDLLCPETYVW
VPIEQCLPSLENSKYCRFNQDPEAVDEDRSTEPDRLQVFHKRAIMPYGVYKKQQ
KDPSEEAAVLQYASLVGQKCSERMLLFRN"

FIGURE 4

```
   1 cgggcggcgc gctgcattgt ggggtggcgg cggcggccgc gctagcgacg cggggccggg
  61 cggctgagcg ttcgcggggc cgaggccatg gctttctggg cgggggggttc gcccagcgtc
 121 gtggactatt tccctagcga ggacttctac cgctgcggct actgcaagaa cgagtcgggc
 181 agccgctcca atggcatgtg ggcacattcc atgacagtac aggattatca ggatctcata
 241 gaccgaggat ggcgaagaag tggaaaatat gtgtacaaac ctgtcatgaa tcaaacatgt
 301 tgtcctcagt acacaataag gtgccgacct ttacaatttc agccttcaaa atctcacaag
 361 aaggttttga aaaaaatgtt gaaatttcta gctaaggggg aggttcccaa aggaagttgt
 421 gaggatgagc ccatggattc cacaatggat gatgctgttg cgggtgactt tgcattgata
 481 aataaactgg atatacagtg tgatcttaaa acactcagtg atgacatcaa agagagttta
 541 gagagtgaag gaaaaaattc aaagaaagaa gaacctcagg aattacttca gtcacaagat
 601 ttcgtaggag agaagttggg ctctggtgaa ccgtcacatt cagttaaagt tcacacagtt
 661 cctaagccag gcaaaggggc tgatttgagt aagcctccat gtcgaaaagc aaggaaatc
 721 cggaaagaaa ggaaaaggtt aaaactaatg cagcagaacc cagctggaga acttgagggt
 781 ttccaggctc aaggtcaccc accatctttg tttccaccaa aggctaaatc caaccagcca
 841 aaatcactcg aagatttaat ttttgagtct ttaccagaga atgcatcaca caagttagag
 901 gtgagggtgg tgagatcatc tccaccaagt tcgcagttca aagccacact tctggagtct
 961 taccaggtct ataaacgtta ccagatggtt attcacaaga acccacctga tacgccaacc
1021 gaaagccagt tcacaagatt cctttgcagt tcacccttgg aggcagagac tccccctaat
1081 gggccagatt gtggctatgg ctcctttcac cagcagtact ggcttgacgg aaagatcatt
1141 gctgtggggg tgattgacat cctcccaaac tgtgtatcat ctgtgtattt gtactacgat
1201 cctgattatt cgttttttgtc tttgggcgtc tactctgcac tacgagaaat tgcttttact
1261 aggcagcttc atgagaaaac ttctcaactc agctattatt atatgggttt ctacattcat
1321 tcatgtccca agatgaaata taagggtcag tatagacctt ctgatttgct gtgccctgag
1381 acatatgttt gggtacccat tgagcaatgc ctgccttcac ttgaaaactc caagtactgc
1441 cgtttcaacc aggacccaga agcagtggat gaggatcgca gtacgaaacc tgaccgattg
1501 caggtgtttc acaagagagc catcatgcct tacggtgttt ataagaaaca gcagaaagac
1561 ccaagtgagg aggctgctgt tctgcagtac gccagcctgg tggggcagaa gtgctccgag
1621 cggatgctgc tgttcagaaa ctgacctgtt cacctctgcc gggaagttcc tgtgttgtgc
1681 tgatgatttg tgccaggata catattcagt acctgtgggg aaataactgt caccacccac
1741 aaattagaca tttttattt tgactatcta tggcttttaa aaaatatttt gtggcaatgt
1801 atctgtgaga atctcatagt taatataaag attttaaaac tgcattatga cctagccccc
1861 ataattggga tttatcattt tggaggattc tttctagagc aagatatgct caaattctcc
1921 tgtttgtatt ttgtaaaatg aagaagtgaa tctaagtaac ttaatcacag ttgtgcattt
1981 ttttttggttc tgttagagaa attaaaacag actgtttcct caggcccatt ttaaactgaa
2041 cttatgctag gaaaccttaa gtatggggaa ggtagaaagt tcatttcatc acttagaaaa
2101 tatgtcttct caagaacaaa actgtgctg
```

MODULATION OF ANGIOGENESIS THROUGH TARGETING OF ARGINYL TRANSFERASE (ATE1)

CROSS REFERENCE TO RELATED APPLICATION(S)

This application is a divisional of U.S. application Ser. No. 10/394,765, filed Mar. 21, 2003 now abandoned, which claims the benefit under 35 U.S.C. § 119(e) to U.S. Application Ser. No. 60/366,207, filed Mar. 21, 2002, now abandoned and U.S. Application Ser. No. 60/366,218, filed Mar. 21, 2002, now abandoned. The disclosure of each of the prior applications is considered part of and is incorporated by reference in the disclosure of this application.

GOVERNMENT INTERESTS

This invention was made in part with government support under Grant No. GM31530 awarded by the National Institutes of Health. The United States government may have certain rights in this invention.

FIELD OF THE INVENTION

The invention relates generally to methods of identification of modulators of angiogenesis and more specifically to modulation of N-terminal arginyl transferase activity.

BACKGROUND INFORMATION

Figure 1A:
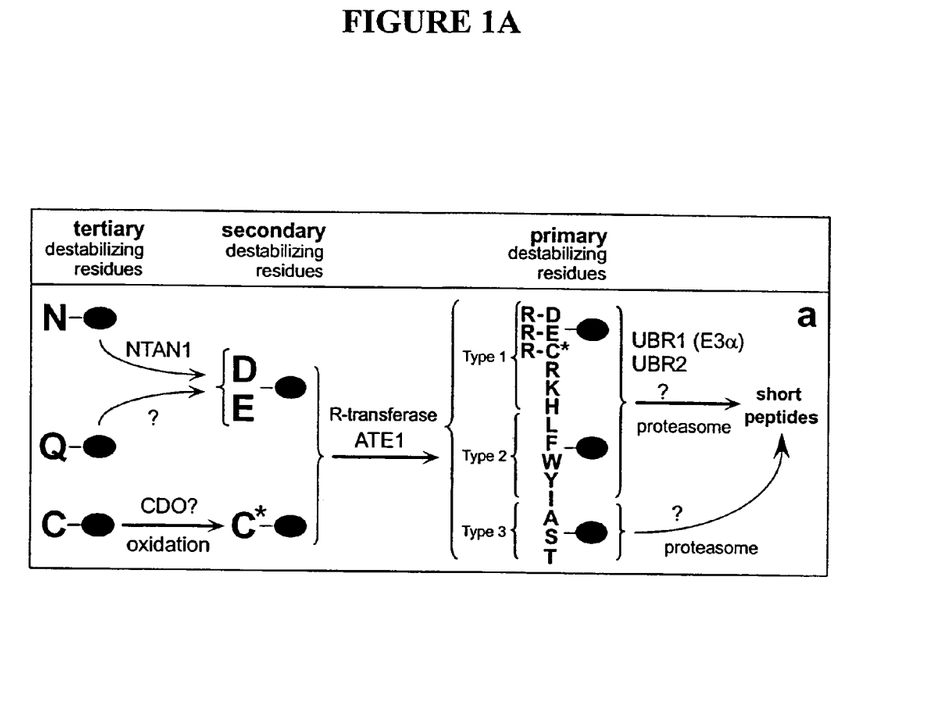
FIG. 1A. N-terminal residues are indicated by single-letter abbreviations for amino acids. Ovals denote the rest of a protein substrate. Type 1 and type 2 primary destabilizing N-terminal residues, Arg, Lys, His, Phe, Leu, Trp, Tyr, and Ile, are recognized by functionally overlapping Ub ligases (E3s) that include UBR1 (E3α) and UBR2. N-terminal Ala, Ser and Thr are recognized by a distinct, unidentified E3.

Substrates of the ubiquitin (Ub)-dependent N-end rule pathway include proteins with destabilizing N-terminal residues. A set of amino acids that are destabilizing in a given cell yields a rule, called the N-end rule, which relates the in vivo half-life of a protein to the identity of its N-terminal residue. The essential component of a degradation signal called the N-degron is a destabilizing N-terminal residue of a protein. Variants of the N-end rule pathway are present in all organisms examined, from animals and plants to fungi and prokaryotes (FIG. 1A). In eukaryotes, an N-degron of a protein consists of a destabilizing N-terminal residue and an internal lysine, the latter being the site of formation of a substrate-linked multi-Ub chain. The N-end rule has a hierarchic structure (FIG. 1A). N-terminal Asn and Gln are tertiary destabilizing residues in that they function through their deamidation, by N-terminal amidohydrolases, to yield the secondary destabilizing residues Asp and Glu. The activity of N-terminal Asp and Glu requires their conjugation, by ATE1-encoded Arg-tRNA-protein transferases (R-transferases), to Arg, one of the primary destabilizing residues. The latter are recognized by the E3 (Ub ligase) components of the N-end rule pathway (FIG. 1A). In mammals, the set of destabilizing residues that function through their arginylation contains not only Asp and Glu but also Cys, which is a stabilizing (non-arginylated) residue in the yeast *Saccharomyces cerevisiae*. The known species of mammalian R-transferase, ATE1-1 and ATE1-2, are produced through alternative splicing of ATE1 pre-mRNA, and have the same substrate specificity as the yeast R-transferase, they arginylate N-terminal Asp or Glu, but cannot arginylate N-terminal Cys.

Angiogenesis is the growth of new blood vessels. Generally in the body, a balance of angiogenesis growth factors and angiogenesis inhibitors keeps this process of blood vessel growth under control. However, a lack or excess of either angiogenesis growth factors or angiogenesis inhibitors can cause undesired growth of blood vessels or a failure to produce blood vessels.

SUMMARY OF THE INVENTION

The present invention is based on the seminal discovery that ATE1 has an important role in angiogenesis, a role that has not been previously described.

In one embodiment, the invention is directed to a method of modulating angiogenesis in a subject. The method of the invention includes administering a modulator of N-terminal protein arginylation to a subject.

In another embodiment, the invention provides a method of identifying a modulator of N-terminal arginylation activity. The method includes providing a cell that expresses a reporter protein with an N-terminal aspartic acid, glutamic acid or cysteine residue. The half-life of the reporter protein is affected by arginylation of the N-terminal protein. The cell is contacted with one or more potential modulators of N-terminal arginylation activity. Then the level of the reporter protein expressed in the presence and absence of the modulator is measured. A change in the level of reporter protein expressed is indicative of modulation of N-terminal arginylation activity. Such a change may be an increase in expression or a decrease in expression. The level of reporter protein may be indicative of the level of protein expressed or may be indicative of the half life of the reporter. In another embodiment, the method further includes providing a second cell that expresses a second reporter protein, where the half-life of the second reporter protein is affected by N-terminal arginylation of the protein and contacting at least one potential modulator of ATE1 gene product activity with the second cell. The level of second reporter protein expressed within the second cell relative to the level of reporter protein expressed within the first cell is then determined. The invention also provides a modulator of N-terminal arginylation activity identified by the above method of the invention.

In still another embodiment, the invention provides an in vitro method of screening for modulators of N-terminal arginylation activity by providing an incubation mixture of protein substrate, ATE1 arginyl transferase source, and at least one potential modulator of ATE1 arginyl transferase activity. The level of arginylation of the peptide substrate is determined in the presence and absence of the modulator, where a change in the level of arginylation of the peptide substrate is indicative of modulation of N-terminal arginylation activity. Such a change may be an increase in expression or a decrease in level of oxidation. The invention also provides a modulator of N-terminal arginylation activity identified by the above method of the invention.

In yet another embodiment the invention is directed to a method of treating an angiogenesis-related disorder in a subject including administering a modulator of angiogenesis to the subject. The administration of the method treats the angiogenesis-related disorder in the subject.

The invention also includes a modulator identified by a method of the invention.

BRIEF DESCRIPTION OF THE DRAWINGS

FIG. 1B. Construction of ATE1$^{-/-}$ mice. Top, a map of the ~20 kb 5'-proximal region of the ~274 kb mouse ATE1 gene. Middle, the knockout (KO) vector. Bottom, the deletiondisruption ATE1$^{-/-}$ allele. Solid vertical rectangles, solid and wavy horizontal lines denote, respectively, the exons, the mouse DNA and the pBR322 DNA. The directions of transcription of NLS-lacZ (NLS-βgal), neo (neomycin), and tk (thymidine kinase) are indicated by arrows. H, HindIII; N, NcoI; X, XhoI; B, BamHI.

FIG. 1C. Northern analysis. Electrophoresed total RNA from E13.5 embryos was hybridized with cDNA probes specific for the deleted region of ATE1 cDNA (nt 132-357, Acc. #AF079096) (upper panel), and with β-actin cDNA (lower panel).

FIG. 2A shows quantitation of results of the stabilization of N-end rule substrates in mouse ATE1$^{-/-}$ cells, and oxidation-arginylation of N-terminal cysteine. ATE1$^{+/+}$ and ATE1$^{-/-}$ EF cells were transfected with plasmids expressing $^f$DHFR$^h$-Ub$^{R48}$-X-nsP4$^f$, whose cleavage yielded the $^f$DHFR$^h$-Ub$^{R48}$ reference protein, denoted as DHFR, and X-nsP4$^f$ test proteins (X=Met, Arg, Asp, Glu, Cys), denoted as X-nsP4. Cells were pulse-labeled for 10 min with $^{35}$S-methionine, and chased for 1 and 2 hr. For each time point, the ratio of $^{35}$S in X-nsP4$^f$ (X=Arg, Asp, Glu, Cys) to $^{35}$S in the $^f$DHFR-Ub$^{R48}$ reference protein at the same time point, was plotted as the percentage of this ratio relative to that for Met-nsP4$^f$ (which bore a stabilizing N-terminal residue) at time 0. Open and closed symbols: +/+ and ATE1$^{-/-}$ cells, respectively. △, ▲, Met-nsP4$^f$; ○, ●, Arg-nsP4$^f$; □, ■, Asp-nsP4$^f$; ▽, ▼, Glu-nsP4$^f$; ◇, ◆, Cys-nsP4$^f$.

FIG. 4 provides the nucleotide sequence of human ATE1, GenBank Accession number: XM_052026.

DETAILED DESCRIPTION OF THE INVENTION

Methods are provided herein, based on the discovery that ATE1 has an important role in angiogenesis, a role that had not been previously described. In particular, the invention provides methods for modulating angiogenisis in a subject by providing a therapeutically effective amount of a modulator of arginyl transferase activity. The invention described herein provides screening methods for modulators of N-terminal protein arginylation or the ATE1 gene product.

As used herein, the term "modulate" or "modulation" is used with regard to modulation of activity. In particular, the present invention provides modulators of arginyl transferase activity or ATE1. As used herein, modulate refers to changing the normal activity. Modulation may be inhibition of an activity or stimulation of the same.

As used herein, the term "angiogenesis" is used to refer to the growth of new blood vessels. Accordingly, an "angiogenesis-related disorder" is a disorder in which the activity of angiogenesis is altered. Such diseases may be completely caused by angiogenesis or may be exacerbated by angiogenesis activity. Angiogenesis-related disorders due to excessive angiogenesis may include, but are not limited to, cancer, tumors, rheumatoid arthritis, psoriasis, rosacea and metastasis of cancerous cells. Angiogenesis-related disorders due to insufficient angiogenesis may include, but are not limited to, coronary artery disease, stroke, ulcers and delayed wound healing.

In one embodiment, the invention provides methods for screening for modulators of N-terminal arginyl transferase activity, in which one or more potential modulators of N-terminal arginyl transferase are contacted with a first cell. The cell expresses a first reporter protein having an N-terminal aspartic acid, glutamic acid or cysteine residue. The level of said first reporter protein present is then determined in the cell either directly or through an indirect means. The level of reporter protein may be indicative of the level of protein expressed or may be indicative of the half life of the reporter. In another embodiment of the invention, the expression of the reporter protein is inducible.

The reporter protein is selected such that it has a relatively short half-life in the cell. Generally, the reporter protein has a half-life in the first cell of less than about an hour in the absence of a modulator. The reporter protein can have a half-life in the first cell of less than about 10 minutes in the absence of the modulator.

In one embodiment of the invention, the reporter protein is expressed as a cleavable fusion protein. The cleavable fusion protein can have an ubiquitin domain functionally linked to the reporter protein. In an appropriate cell, the ubiquitin domain is rapidly cleaved by one of several deubiquitylating enzymes.

In yet another embodiment of the invention, the screening methods described can be accomplished in a variety of cells, including in a cultured mammalian cell, a yeast cell or a bacterial cell.

The first type of screen for inhibitors of ATE1-mediated N-terminal arginylation can be carried in the setting of either mammalian cells in culture or yeast (*S. cerevisiae*) cells in culture. Note that, at least in mammalian cells and yeast, the ATE1-encoded R-transferases are solely responsible for N-terminal arginylation. The logic of either yeast- or mammalian cells-based screens is essentially the same. The advantage of a yeast-based screen is the ease of handling and analyzing yeast cell cultures; the disadvantage is that potential inhibitors of R-transferase that would cross the plasma membrane of mammalian cells may be incapable of gaining entry into yeast cells, given substantial differences in the permeability (and transport) properties of the plasma membrane between yeast and mammals. A mammalian cells-based screen is preferred, since the sought inhibitors would be intended for use in mammals. The screen: a mammalian (mouse or human) cell line is set up that expresses a short-lived reporter whose ubiquitin-dependent degradation by the N-end rule pathway involves N-terminal arginylation. Such a reporter would be a protein with either a genetically selectable or "screenable" (visually detectable) influence on the test cell culture.

A number of classes of reporter proteins are suitable for use with the methods of the invention. For example, the reporter protein can be a genetically selectable marker protein, and the relative level of the reporter protein in the presence and absence of a modulator can accomplished indirectly through a selective genetic screen which requires the presence of said reporter protein for survival of said first cell. In such an example, a modulator which inhibits the arginyl transferase activity would therefore lengthen the half-life of the reporter protein. For example, the selectable marker protein can be an antibiotic resistance protein. In one such example, the reporter protein is designed to be short-lived in a cell, the cell will be relatively sensitive to the relevant antibiotic. By contrast, if the protein is made long-lived in vivo, for example through the inhibition of a proteolytic pathway, and more specifically through inhibition of the arginyl transferase activity, that normally destroys this protein, its steady-state level would, by definition, increase, and the cell would become resistant to the same dose of antibiotic. This readout would enable a selection-based screen. A number of reporter proteins that confer antibiotic resistance are known to those skilled in the art.

Detection of the relative abundance of the reporter protein also can be accomplished by more direct means. For example, the reporter protein can be a screenable reporter protein. Such proteins may include, but are not limited to Green Fluorescent Protein (GFP) and *E. coli* β-galactosidase (βgal). A number of fluorescent proteins are known to those of skill in the art. These proteins, if expressed in a cell, can be detected either through their fluorescence (GFP) or through their enzymatic activity (βgal). The suitable reporter protein can be expressed in the cell type used for the assay and has sufficient fluorescence intensity to be detected within the cell at the appropriate concentrations. Making a reporter of this class short-lived in vivo would strongly diminish its steady-state level in a cell. If degradation of such a short-lived reporter is inhibited, its steady-state level will rise, enabling the detection of reporter. The level of protein present can be determined using fluorescence detection, for example, using a fluorometer or fluorescence microscope. The relative amount of fluorescence can be compared between cells treated with a potential modulator versus no treatment. Similarly, the reporter protein can be a light-generating protein, for example, luciferase. The amount of light produced can be measured and compared in cells treated with a modulator and in untreated cells.

The level of reporter protein present can also be determined enzymatically. For example, enzymes capable of making a calorimetric change in a substrate, can be detected indirectly. One such protein, *E. coli* β-galactosidase (βgal), can be detected through a calorimetric change it causes in the substrate X-gal (5-bromo-4-chloro-3-indolyl-β-D-galactosidase). Making a reporter of this class short-lived in vivo would strongly diminish its steady-state level in a cell. If degradation of such a short-lived reporter is inhibited, its steady-state level will rise, enabling the detection of the reporter protein (through an enzymatic reaction).

Other reporter protein systems are known to one of skill in the art and can be applied to the methods of the invention. As will be apparent to one of skill in the art, the invention is not limited to those currently known, but can also be extended to newly discovered reporter protein systems.

The invention also provides modulators of N-terminal arginyl transferase activity. In summary, the invention provides methods for identifying modulators of angiogenesis that operate by altering the enzymatic activity of the N-terminal arginylation of a polypeptide.

According to another embodiment of the invention, the screening methods can include additional features, including contacting the potential modulators of angiogenesis with a second cell, wherein the second cell expresses a second reporter protein having an N-terminal arginine residue and determining the level of expression of the second reporter protein relative to said first reporter protein. These settings serve as negative-controls for those in which a reporter protein contains a N-terminal aspartic acid, glutamic acid or cysteine residue. According to the invention, the second cell can be the same cell as the first cell (i.e., a cell expressing both the first reporter protein and the second reporter protein) or can be a different cell (i.e., one not expressing the first reporter protein). Such a screening method allows for the selection of modulators specific for the N-terminal arginylation activity that do not inhibit the rest of the N-end rule pathway, including subsequent protein degradation steps. According to this embodiment of the invention, a desired modulator of N-terminal arginyl transferase activity would alter the relative abundance of the N-terminal aspartic acid, glutamic acid or cysteine residue containing first reporter protein, but would not significantly alter the relative abundance of the second reporter protein having an N-terminal arginine residue. In one embodiment of such an assay system, the first reporter protein and the second reporter proteins are fluorescent proteins having distinct spectral properties.

In one embodiment of the invention, the screen is carried out with a GFP-based reporter. Mammalian cells growing in microtiter plates and expressing Asp-GFP that is designed to be N-terminally arginylated and rapidly destroyed by the N-end rule pathway, are exposed to a library of potential inhibitors of R-transferase (one tested compound per well, with different concentrations of a compound in adjacent wells). After incubation with the library of compounds, the microtiter plates are scanned by plate fluorimeter to detect wells where the levels of Asp-GFP increased. Compounds of the library that caused the increase of GFP level are then re-tested in control assays, to identify those among them that act by inhibiting N-terminal arginylation. One way to do that is to add these compounds, one at a time, to an otherwise identical mammalian cell culture that expresses Arg-GFP, a reporter identical to Asp-GFP except for Arg instead of Asp at its N-terminus. Such a reporter would be degraded by the N-end rule pathway in arginylation-independent manner. Any compound that inhibits degradation of Asp-GFP but does not significantly inhibit degradation of Arg-GFP would be, immediately, a strong candidate for a specific inhibitor of R-transferase.

Confirmation of inhibition of R-transferase may then be obtained in at least two ways: 1) in vivo, by isolating Asp-GFP from cells treated with inhibitor versus control (untreated) cells, and N-terminally sequencing Asp-GFP from these two sources, to determine whether its N-terminal arginylation was, in fact, inhibited in vivo by the compound in question; or 2) a direct enzymatic assay with purified R-transferase and test the identified compound or compounds (identified through initial screen) for inhibition of N-terminal arginylation of a model substrate in vitro.

In another embodiment of the invention, the screen is carried out with a GFP-based reporter. Mammalian cells growing in microtiter plates and expressing Asp-GFP, that is designed to be N-terminally arginylated and rapidly destroyed by the N-end rule pathway, are exposed to a library of potential inhibitors of ATE1 (one tested compound per well, with different concentrations of a compound in adjacent wells). After incubation with the library of compounds, the microtiter plates are scanned by plate fluorimeter to detect wells where the levels of Asp-GFP increased. Compounds of the library that caused the increase of GFP level are then re-tested in control assays, to identify those among them that act by inhibiting arginylation of the N-terminal aspartic acid residue. In one embodiment, the screen can differentiate between compounds that act on the arginyl transferase versus the rest of the N-end rule pathway, including the rest of its degradation pathway (e.g., proteasome inhibition). For example, these compounds can be added, one at a time, to an otherwise identical mammalian cell culture that expresses Arg-GFP, a reporter identical to Asp-GFP except having Arg residue at its N-terminus. Such a reporter would be degraded by the N-end rule pathway in arginylation-independent manner; and therefore it would not require the action of the arginylation activity. Any compound that inhibits degradation of Asp-GFP but does not significantly inhibit degradation of Arg-GFP would be, immediately, a strong candidate for a specific inhibitor of R-transferase.

Confirmation of inhibition of ATE1 may then be obtained in at least two ways: 1) in vivo, by isolating Asp-GFP from cells treated with inhibitor versus control (untreated) cells, and N-terminally sequencing Asp-GFP from these two sources, to determine whether its N-terminal arginylation was, in fact, inhibited in vivo by the compound in question; pr 2) direct enzymatic assay with purified AET1 and test the identified compound or compounds (identified through initial screen) for inhibition of N-terminal arginylation of a model substrate in vitro.

To carry out a screen for inhibitors of N-terminal arginylation, a reporter of either class will have to be extended N-terminally with a sequence of amino acid residues known as the N-degron, a class of degradation signals (degrons) recognized by the ubiquitin-dependent N-end rule pathway of protein degradation. A particular class of N-degrons that would require N-terminal arginylation for its activity would have aspartate (Asp) as the N-terminal residue of the reporter, since asp is one of three residues arginylated by the N-end rule pathway, by R-transferase, prior to reporter's degradation. Previous extensive work by this and other laboratories made the construction of N-degron-equipped reporters a well-developed art known to researchers in the field.

A number of techniques are available to express a reporter protein having a desired N-terminal residue. Universally, translated proteins are initiated with an amino-terminal methionine residue. Processing of the protein by various peptidases can expose an internal residue as an amino-terminal residue. One such technique involves expressing a fusion protein having a ubiquitin domain and a reporter protein domain. The ubiquitin domain is rapidly cleaved from the fusion protein by a class of enzymes known as the deubiquitinylating enzymes (DUBs). This strategy is well known to one of skill in the art and is taught, for example, in references 3, 5 and 16, which are incorporated herein by reference in their entireties.

The in vitro methods for screening for modulators of angiogenesis that act through modulation of the N-terminal arginylation activity can be performed in a variety of formats. In one such method, a substrate peptide having an N-terminal aspartic acid or glutamic acid residue is incubated with one or more potential modulators of ATE1 arginyl transferase activity as well as an ATE1 arginyl transferase, and the level of arginylation of the peptide substrate is determined. The arginyl transferase can be provided as a cellular extract or can be provided as a purified enzyme. The reaction mixture can contain any necessary cofactors, for example, ATP, and arginyl-tRNA. The level of N-terminal arginylation of the peptide substrate can be determined by any suitable method, including for example, by electrophoresis, including capillary electrophoresis, by chromatography, including HPLC and TLC, by mass spectroscopy, by immunoassay. The degree or rate of N-terminal arginylation can be compared using such techniques, or combinations of techniques to determine the impact of a modulator of N-terminal arginylation activity. The type of detection used in such a scheme can be determined by one of skill in the art and will be chosen as to be compatible with the type of separation used. For example, when the technique to be used is HPLC, detection can be UV detection.

In one embodiment of the invention, the peptide substrate is immobilized, for example to the surface of a microtiter plate. In such an embodiment, the level of arginylation can be determined by reaction with an antibody that can distinguish between the substrate peptide and an arginylated form of the substrate peptide. A number of suitable detection schemes are known to one of skill in the art of immunological assays, including directly linking the antibody to a colorimetric or fluorescent moiety, or using a sandwich type assay, in which the detection means is provided by a second protein, typically an antibody which binds to the first antibody. Selective antibodies of the type necessary for such an assay can be generated by a number of techniques well known to one of skill in the art, including for example subtractive immunization.

In one embodiment, the screen would consist of purified R-transferase added to wells of microtiter plates. The R-transferase may be, but is not limited to, human or mouse. An arginylation assay is carried out in these wells either in the absence or the presence of a library of compounds (one compound per well), and the plate is screened, using either calorimetric or fluorescence-based readout, for the wells where arginylation was inhibited. The readout can be, for example, a short peptide bearing N-terminal Asp, which is arginylated by R-transferase in this in vitro assay. This peptide will have to be immobilized to bottoms of wells, a straightforward arrangement. The assay, in each well, would also contain R-transferase, ATP, Arg-tRNA and other necessary (and well known) components of arginylation reaction. A non-arginylated version of this peptide would react with a separately prepared antibody to the peptide that recognizes, among its other determinants, the peptide's (unmodified) N-terminus. Arginylation of this peptide would extinguish the recognition of peptide by this antibody, thereby providing the required readout. Other feasible variations of this assay are within the capacity of one of skill in the art.

In still another embodiment, the invention provides modulators identified by any of the methods of the invention.

In another embodiment the invention provides methods for modulating angiogenesis in a subject, comprising administering to a subject a modulator of the arginyl transferase activity of an ATE1 gene product. In one embodiment, the subject is a mammal, such as a human or a mouse. Inhibitors of N-terminal arginyl transferase activity can be used to treat patients, for example, who are in need of inhibited angiogenic activity, for example, those with tumors.

In still another embodiment of the invention, a method of treating an angiogenesis-related disorder is provided. The method involves administering a modulator of angiogenesis to a subject, thereby treating the angiogenesis-related disorder in the subject. Such a modulator may inhibit N-terminal protein arginylation or arginyl transferase or ATE1 gene product activity. The subject may be a mammal. The angiogenesis modulator may inhibit or stimulate angiogenesis in the subject, thereby treating the angiogenesis-related disorder. Angiogenesis-related disorders treated by this method of the invention may include, but are not limited to: cancer, tumors, rheumatoid arthritis, psoriasis, rosacea, metastasis of cancerous cells, coronary artery disease, stroke, ulcers and delayed wound healing.

In a preferred embodiment, the potential modulators are small organic compounds, that is compounds having a molecular weight of less than about 1,000. Such compounds are available from natural sources including plant, bacterial, and fungal extracts, and from techniques such as combinatorial chemistry and synthetic chemistry in general. One of skill in the art will recognize that libraries of compounds are commercially available.

The following examples are intended to illustrate but not limit the invention.

EXAMPLE 1

Generation of ATE+/− and ATE1$^{-/-}$ Mice

This example describes the generation of the mice lacking the ATE1 activity. These mice serve as a model for the activity of an inhibitor of ATE1 activity (either an enzymatic inhibitor, or an inhibitor which lowers the level of expression of the ATE1 gene, for example, antisense oligonucleotides directed to the ATE1 mRNA).

Mouse ATE1 was isolated using screening, with an ATE1 cDNA fragment (nt 638-1,491), a BAC library (Genome Systems) from 129/SvJ ES mouse cells. The exon/intron organization of the first ~20 kb of ATE1 was determined using exon-specific PCR primers to produce genomic DNA fragments flanked by exons. The targeting vector (FIG. 1B) was linearized with HindIII and electroporated into CJ7 embryonic stem (ES) cells, followed by selection and identification of the correctly targeted ATE1$^{+/-}$ ES cell clones with normal karyotype. Standard techniques were then used to produce chimeric and ATE1$^{-/-}$ mice. Phenotypes of ATE1$^{-/-}$ embryos were observed mainly with mice of the C57BL/6J-129SvEv (mixed) background, and confirmed in the 129SvEv (inbred) background. RT-PCR, Southern and Northern analyses, and PCR-mediated genotyping of embryos and pups were performed as described.

Heterozygous (ATE1$^{+/-}$) mice were viable and apparently normal. Intercrosses of ATE1$^{+/-}$ mice yielded the expected frequencies of +/+ and ATE1$^{+/-}$ pups, but no ATE1$^{-/-}$ mice were recovered amongst either 954 $F_2$-generation pups of the C57BL/6J-129SvEv (mixed) background or 267 $F_2$-generation pups of the 129SvEv (inbred) background. Timed intercrosses of ATE1$^{+/-}$ mice were used to determine that ATE1$^{-/-}$ embryos were present at approximately the expected (25%) frequency up to ~E13.5, but virtually no ATE1$^{-/-}$ embryos were recovered alive by E17. Until E12.5, ATE1$^{-/-}$ embryos appeared to be morphologically normal; however, their growth stopped during E13.5-E15.5. By E14.5-E15.5, ~50% of ATE1$^{-/-}$ embryos were still alive, but growth-retarded. Live E14.5-E15.5 embryos were capable of opening their mouths and flexing their bodies, suggesting the absence of gross neuromuscular defects. Sections through E13.5 ATE1$^{-/-}$ embryos indicated the presence and apparently normal appearance of major organs, except for the phenotypes described below in Example 3.

EXAMPLE 2

Expression of ATE1-Allele

Figure 1B:
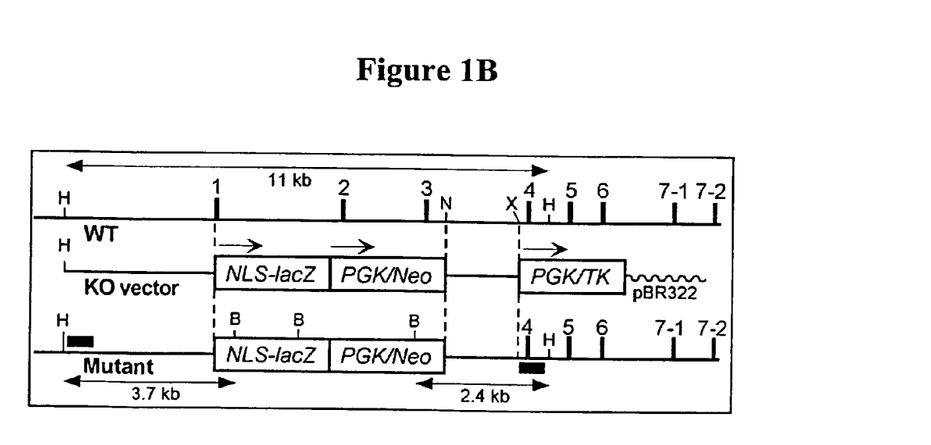
Figure 1C:
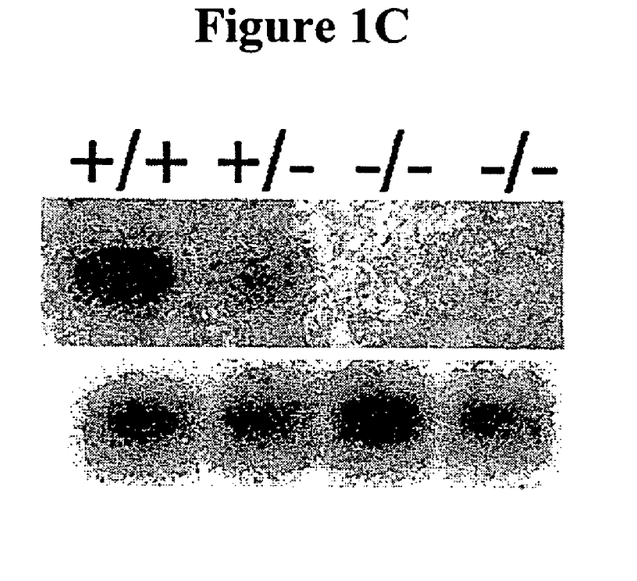
Figure 1D:
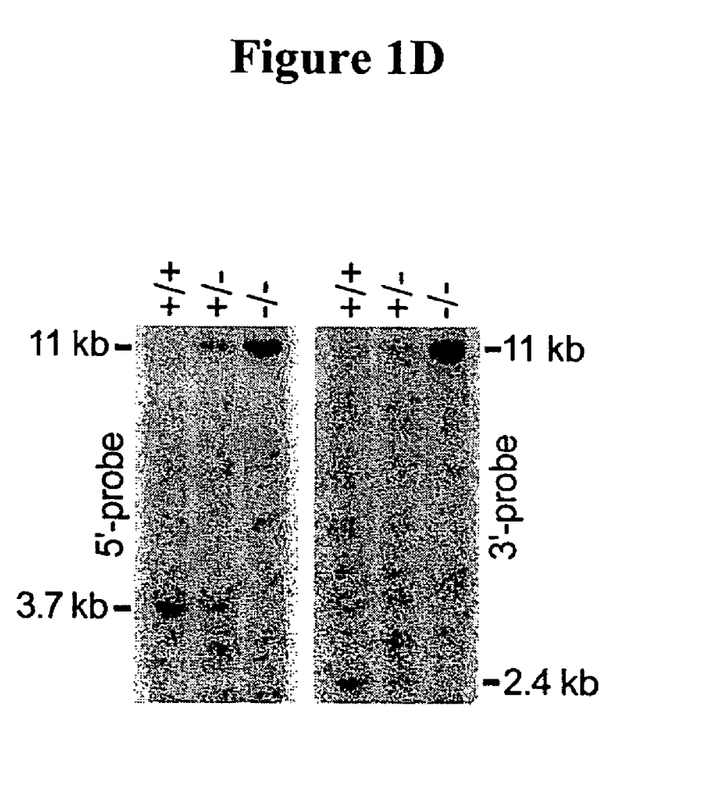
FIG. 1D. Southern analysis of ATE1, using a 0.57 kb 5'-probe, a 0.45 kb 3'-probe (indicated by black rectangles in FIG. 1B, and HindIII/BamHI-cut genomic DNA from +/+, ATE1$^{+/-}$, and ATE1$^{-/-}$ E13.5 embryos.

The ATE1$^-$ allele was marked with NLS-β-galactosidase (hereafter βgal), expressed from the ATE1 promoter (FIG. 1B). During E9.5-E12.5, the expression of ATE1 (βgal) was high in the neural tube, including the floor plate, motor neurons, and the neural fold. ATE1 was also expressed in dorsal root ganglia, sympathetic ganglia and notochord, and in neurons that regulate blood vessels; the latter examples included sympathetic trunks between midline dorsal aorta and subcardinal vein, and a ganglion near the primary head vein. ATE1 was also expressed in sharply delineated subsets of myotomal cells in each somite, in the mesonephric vesicles (kidney precursor), in the gut, in specific areas of the eye primordium, at the tips of limb buds, in the endodermal layer of the yolk sac (but not in its mesodermal layer), and in specific areas of embryonic heart, including trabeculae, endocardial cushion, aortic valve, and aorta.

EXAMPLE 3

Angiogenic Defects of ATE1−/− Mice

ATE1$^{-/-}$ embryos (and yolk sacs) were pale in comparison to their +/+ and ATE1$^{+/-}$ littermates, had thinner blood vessels and frequent edemas of the skin, with extensive apoptosis of cells in edematous regions. About 40% of live E15.5 ATE1$^{-/-}$ embryos looked nearly normal, except for a significant growth retardation, thinner peripheral vessels and thinner vitelline vessels. The rest (~60%) of live E15.5 ATE1$^{-/-}$ embryos exhibited at least one of the following phenotypes: local hemorrhages, edemas, and abdominal ruptures. Hemorrhages, often massive, at various locations, predominantly in the abdominal cavity and the head, were a consistent feature of ATE1$^{-/-}$ embryos, and the likely proximal cause of their death by E15-E17. Transverse sections of hematoxylin/eosin-stained +/+ and ATE1$^{-/-}$ hearts of E14.5 embryos showed numerous defects. Amongst 13 ATE1$^{-/-}$ hearts (E13.5-E15.5) examined, ~85% had a ventricular septal defect (VSD). The atria of many ATE1$^{-/-}$ hearts were abnormally thin-walled, with sparse trabeculae and a large atrial septal defect (ASD). The right atria of ATE1$^{-/-}$ hearts were often enlarged, resulting in twisted ventricles (data not shown). Amongst 22 ATE1$^{-/-}$ hearts examined (13 extensively and 9 less so), ~90% exhibited hypoplasia of both right and left ventricular myocardium, resembling thin myocardium syndrome. The compact zone (CZ) of left ventricular myocardium was typically 2-3 cells thick, in comparison to 7-10 cells in the myocardium of +/+ littermates. Furthermore, whereas the aorta and pulmonary artery were completely separated by E13.5 in +/+ hearts, ~70% of the examined ATE1$^{-/-}$ hearts (E13.5-E15.5) had persistent truncus arteriosus (PTA), with the common root of aorta and pulmonary artery straddling a large VSD. Formation of the two ventricular chambers involves proliferation and maturation of myocytes in the compact muscular layer, accompanied by trabeculation inside the chamber. The septum is formed through condensation of trabeculae at the interventricular groove, with the medial walls of expanding ventricles fusing together, growing inward, and forming the muscular portion of septum. The above defects of ATE1$^{-/-}$ hearts suggest that the loss of R-transferase activity inhibits proliferation of myocardial cells. In addition, the PTA defect occurs when too few of the neural crest-derived cells populate the cardiac outflow tract, resulting in a failure to separate the common truncal outflow vessel into the aorta and pulmonary artery. Since ATE1 is highly expressed in structures produced by cells originating in the neural crest, the PTA defect of ATE1$^{-/-31}$ hearts suggests that the R-transferase activity is also required for migration and/or differentiation of neural crest-derived myocardial cells.

Vasculogenesis, the de novo formation of blood vessels that yields the primary capillary plexus at early stages of embryogenesis, was apparently normal in E9.5 ATE1$^{-/-}$ embryos, as assayed by staining endothelial cells with anti-PECAM antibody. Standard procedures were used for thin sectioning and staining with hematoxylin/eosin, X-Gal, or anti-PECAM-1 antibody (clone MEC 13.3, Pharmingen). In contrast, the process of subsequent angiogenic remodeling that produces a hierarchic network of mature capillaries and larger vessels, was perturbed in the absence of ATE1, as could be seen, for example, in the vasculature of E13.5 +/+ versus ATE1$^{-/-}$ yolk sacs. The vessels in ATE1$^{-/-}$ sacs often terminated prematurely, and many small vessels remained as a honeycomb-like meshwork of the primary-plexus capillaries, without angiogenic remodeling. The large collecting vessels of ATE1$^{-/-}$ yolk sacs were consistently smaller than their +/+ counterparts, and ATE1$^{-/-}$ microvilli were poorly developed. In addition, the angiogenesis-produced network of blood vessels that normally cross the dorsal midline and that normally sprout from intersegmental artery was suppressed in E9.5 ATE1$^{-/-}$ embryos. An example of impaired angiogenesis in older ATE1$^{-/-}$ embryos was the head's dorsal area at E13.5. This area was a major site of hemorrhages in ATE1$^{-/-}$ embryos. Amongst 13 extensively examined ATE1$^{-/-}$ embryos, only one appeared to have a normal heart; yet, similarly to other ATE1$^{-/-}$ embryos, it exhibited angiogenesis defects in the yolk sac, suggesting that abnormal angiogenic remodeling was not caused by the cardiogenic defects of ATE1$^{-/-}$ embryos. A rigorous deconvolution of causes and effects in this complex setting will require the understanding of molecular circuits involved.

Increased apoptosis, detected using the TUNEL assay, was found in the edematous area of E13.5 ATE1$^{-/-}$ embryo. The TUNEL assay was performed using a kit (Roche) and fluorescein-dUTP.

This example clearly illustrates the importance of the ATE1 gene to the process of angiogenesis. The clear evidence that mice lacking the ATE1 gene shows that inhibitors of ATE1 will also impact angiogenesis in an animal.

EXAMPLE 4

Arginyl Transferase Reactions

For R-transferase assays (FIG. 2B), Ub-X-βgal proteins were purified from *E. coli* carrying pKKUbXβgal plasmids. The R-transferase reaction (50 ml) contained S105 supernatant (0.5 mg of protein per ml) from either EF cells or whole embryos, prepared as described (30), Ub-X-βgal or α-lactalbumin (0.2 mg/ml), *E. coli* tRNA (1 mg/ml), *E. coli* aminoacyl-tRNA synthetases (50 mg/ml), puromycin (0.2 mM), bestatin (0.15 mM), 5 mM MG132 (proteasome inhibitor), 0.4 mM Lys-Ala dipeptide (inhibitor of post-arginylation steps in the N-end rule pathway), 1 mM ATP, 10 mM creatine phosphate, 0.1 M KCl, 5 mM MgCl$_2$, 50 mM β-mercaptoethanol, 50 mM Tris-HCl (pH 8.0) and 0.3 mM $^3$H-arginine (New England Nuclear). The reaction mixture was incubated for 3 hr (2 hr with embryo extracts) at 37° C. A 20 ml sample was precipitated with 10% TCA, and analyzed by SDS-12% PAGE and fluorography.

Figure 2A:
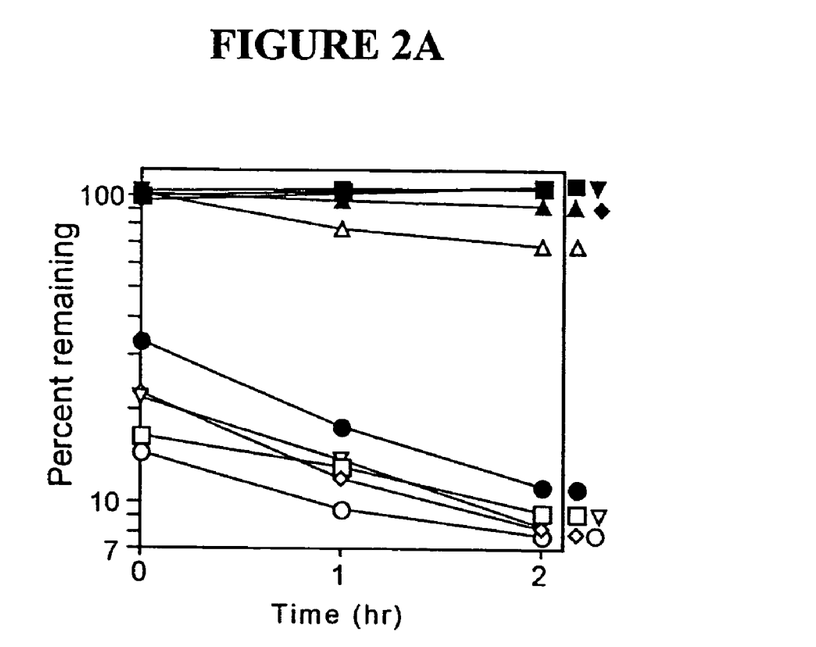
Figure 2B:
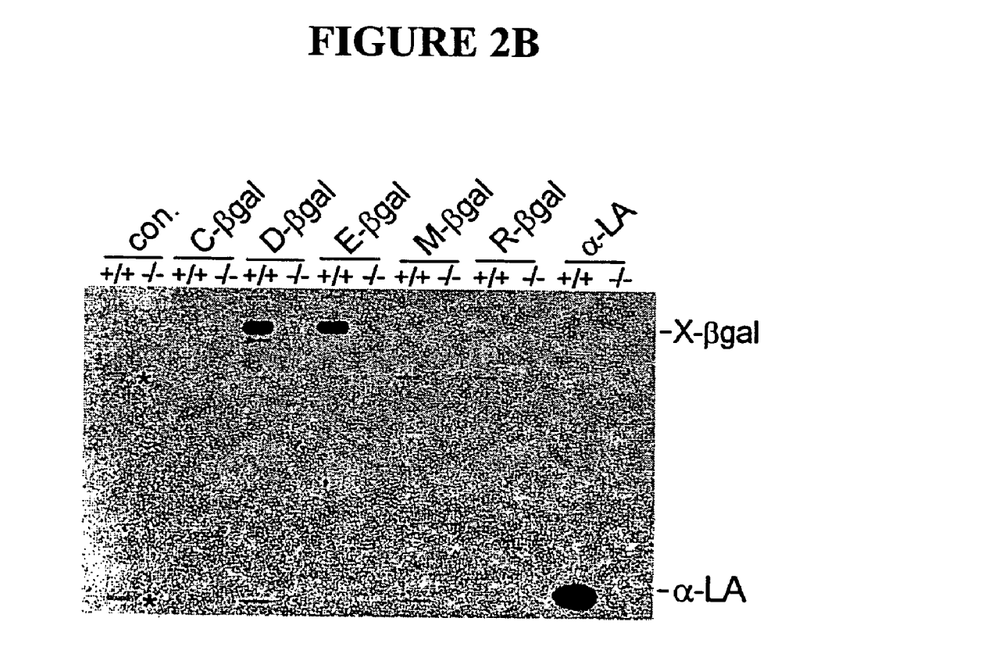
FIG. 2B shows a cell-free assay for mouse R-transferase using $^3$H-Arg, S105 extracts from +/+ and ATE1$^{-/-}$ EF cells, and unlabeled X-βgals (X=Cys, Asp, Glu, Met, Arg) and α-lactalbumin as test substrates. Arginylated test substrates are indicated on the right. Asterisks indicate arginylated endogenous proteins in the extracts.
Figure 2C:
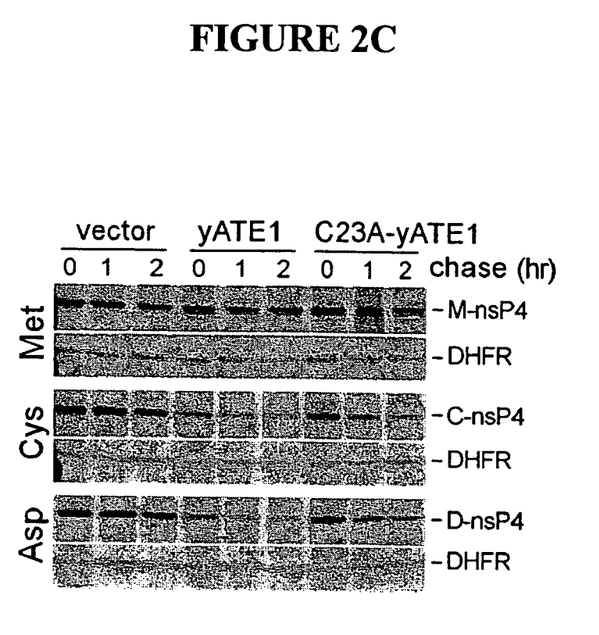
FIGS. 2C and 2D show Mouse ATE1$^{-/-}$ EFs were co-transfected with a plasmid expressing X-nsP4$^f$ and a plasmid expressing either wild-type *S. cerevisiae* ATE1 (pCDNA3yATE1) or its enzymatically impaired mutant (pCDNA3yATE1C23A). Curve designations: Met-nsP4$^f$ coexpressed with either a vector alone (open square), or yeast ATE1 (solid square), or mutant yeast ATE1 (solid black square). Cys-nsP4$^f$: the same except for diamonds instead of squares. Asp-nsP4$^f$: the same except for circles instead of squares.
Figure 2D:
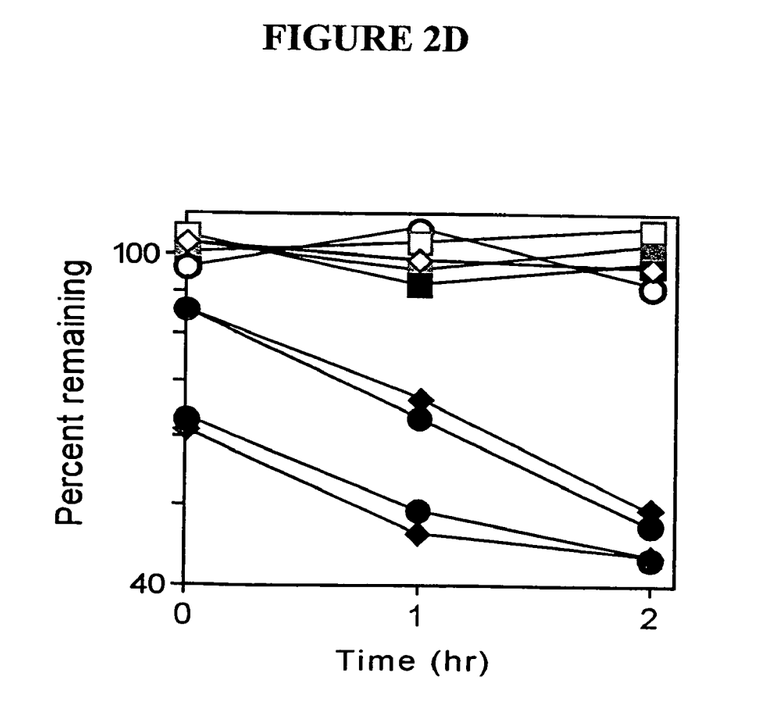
Figure 3:
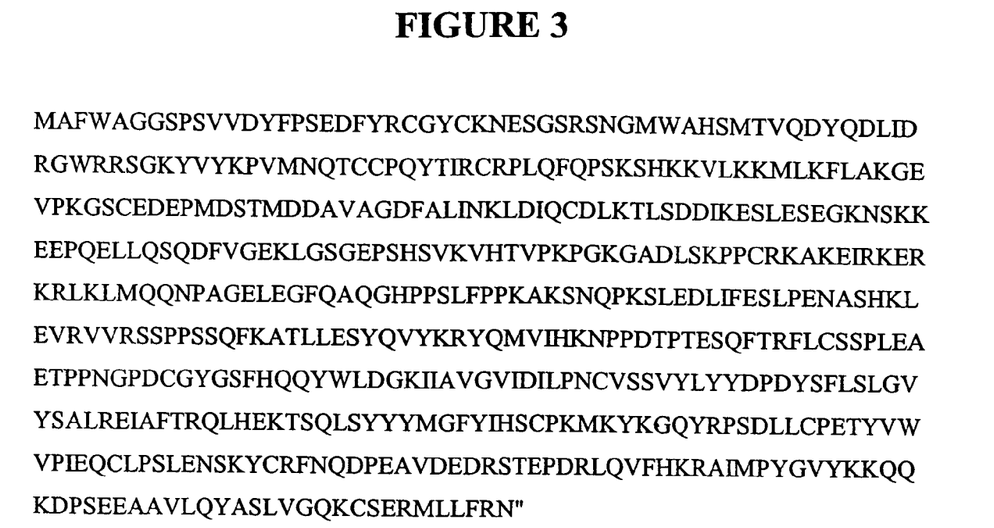
FIG. 3 provides the primary sequence of human ATE1 arginyl transferase protein, GenBank Accession XP_052026. Alternatively spliced versions of ATE1, ATE-1p and ATE1-2p also are known: GenBank Accession numbers AAD12366 and: AAD12367 respectively.

To measure the N-terminal arginylation directly, either purified Ub-X-βgal proteins (X=Met, Arg, Glu, Cys) or purified human α-lactalbumin (bearing N-terminal Glu) were added to +/+ and ATE1$^{-/-}$ EF cell extracts supplemented with ATP, total *E. coli* tRNA and a mixture of *E. coli* aminoacyl-tRNA synthetases. SDS-PAGE and fluorography were used to detect covalent conjugation of $^3$H-Arg to test proteins in these extracts (FIG. 2B). Ub-X-βgals are rapidly deubiquitylated in vivo and in cell-free extracts, yielding X-βgal test proteins. As expected, Asp-βgal, Glu-βgal and α-lactalbumin were arginylated in the extracts from +/+ EF cells, whereas Arg-βgal and Met-βgal, bearing a primary destabilizing and a stabilizing N-terminal residue, respectively, were not arginylated (FIG. 2B). Crucially, no arginylation of Asp-βgal, Glu-βgal and α-lactalbumin could be detected in ATE1$^{-/-}$ EF extracts (FIG. 2B), even after prolonged fluorographic exposures. Identical results were obtained with extracts from +/+ and ATE1$^{-/-}$ embryos. In addition to being consistent with the conclusions from pulse-chase analyses in EF cells, these findings confirmed the absence of R-transferase activity from ATE1$^{-/-}$ embryos.

EXAMPLE 5

Assays in Mouse Embryonic Fibroblasts

Primary mouse EFs were established from E13.5 ATE1$^{-/-}$ and littermate +/+ embryos as described, and immortalized to increase transfection efficiency. Cells were transiently transfected with pcDNA3flagDHFRhaUbXnsP4flag, which expressed fDHFR$^h$-UbR48-X-nsP4$^f$ from the PCMV promoter. Cells were labeled with $^{35}$S-EXPRESS (New England Nuclear) for 10 min at 37° C., followed by a chase for 0, 1, and 2 hr in the presence of cycloheximide, preparation of extracts, precipitation with anti-flag antibody, SDS-10% PAGE, autoradiography, and quantitation using PhosphorImager. In other pulse-chases, ATE1$^{-/-}$ EFs were co-transfected with a plasmid expressing X-nsP4$^f$ (fDHFRh-UbR48-X-nsP4 f) and either pCDNA3yATE1, expressing *S. cerevisiae* ATE1, or pCDNA3yATE1C23A (derived from a plasmid supplied by Dr. C. Pickart, Johns Hopkins University), which expressed ATE1C23SA, bearing Cys→Ala mutation at position 23.

To examine the in vivo degradation of N-end rule substrates in ATE1$^{-/-}$ cells, immortalized embryonic fibroblast (EF) cell lines were established from ATE1$^{-/-}$ and littermate +/+ embryos. The EFs were transiently transfected with plasmids that expressed X-nsP4$^f$, a set of otherwise identical 69K flag-tagged Sindbis virus RNA polymerase proteins bearing different N-terminal residues (FIG. 1A). X-nsP4$^f$ proteins were expressed as parts of $^f$DHFR$^h$-Ub$^{R48}$-X-nsP4$^f$ fusions, the UPR (Ub/protein/reference) constructs, in which the reference moiety $^f$DHFR$^h$-Ub$^{R48}$ contained an epitope-tagged mouse dihydrofolate reductase (DHFR). DHFR$^h$-Ub$^{R48}$-X-nsP4$^f$ is cotranslationally cleaved by deubiquitylating enzymes (DUBs) at the Ub$^{R48}$-X junction, yielding the long-lived $^f$DHFR$^h$-Ub$^{R48}$ reference protein and a test protein X-nsP4$^f$. Through the presence of a "built-in" reference protein, the UPR technique increases the accuracy of pulse-chase assays, and in addition allows the detection of a test protein's degradation during the pulse. As expected, R-transferase substrates were short-lived in +/+ EF cells: more than 90% of pulse-labeled Asp-nsP4$^f$ and Glu-nsP4$^f$ were degraded by 2 hr of chase. In contrast, both Asp-nsP4$^f$ and Glu-nsP4$^f$ were completely stabilized in ATE1$^{-/-}$ cells, whereas Arg-nsP4$^f$, bearing a primary (arginylation-independent) destabilizing N-terminal residue, remained short-lived in these cells. Strikingly, although the mouse ATE1-encoded R-transferases cannot arginylate N-terminal Cys, the normally short-lived Cys-nsP4$^f$ also became long-lived in ATE1$^{-/-}$ EF cells, indicating that ATE1 is required for the arginylation of N-terminal Cys, through a mechanism determined by the inventors to involve a catalytic oxidation of N-terminal cysteine residues.

EXAMPLE 6

Gene Circuits Involving ATE1

To begin a search for mouse genes whose expression is significantly altered in the ATE1$^{-/-}$ background, RT-PCR and Northern analyses were carried out with total RNA from +/+ and littermate ATE1$^{-/-}$ embryos proper, their yolk sacs, and their hearts, using mouse cDNA probes specific for genes that encode the following proteins: NTAN1, UBR1, UBR2 (components of the N-end rule pathway); eHand, ICAM2, GATA6, Nfarc1, dHand, NF1, RXRα, FOG2, GATA4, MEF2c, Neuropilin 1, TEF1, N-myc, RARα, ErbB2 (proteins whose functions include heart development); TIE1, TIE2, FLK1, FLK2, FLT1, FLT4, βH1, GATA1, I1-3R, CD34, VEGF, VEGF-B, VEGF-C, VEGF-D, ANG1, ANG2, ANG3, EfnB1, EfnB2, EfnA1, EphB2 (proteins whose functions include vascular development). No significant differences were detected in the expression of these genes between the ATE1$^{-/-}$ and +/+ genetic backgrounds, making it more likely that the absence of ATE1 impacted a previously undescribed circuit.

The N-end rule is implicated in a variety of physiological processes, including angiogenesis. Mice lacking the gene ATE1 were shown to have extensive defects in angiogenic development. Because of the importance of the arginylation pathway to angiogenesis, inhibitors of the N-terminal arginyl transferase activity can be used as anti-angiogenic compounds for the treatment of tumors, and particularly of solid tumors.

Recent studies have identified the mammalian Met-aminopeptidase MetAP2 as the target of fumagillin and related inhibitors of angiogenesis. Upon inhibition of MetAP2, some intracellular proteins partially retain their N-terminal Met residues. The N-terminal Met-Cys bond (but neither Met-Asp nor Met-Glu) can be cleaved by MetAP2. The results suggest that metabolic stabilization of an arginylation-dependent N-end rule substrate(s) in mouse ATE1$^{-/-}$ cells causes angiogenic and cardiogenic defects. Thus, one possibility is that fumagillin and related drugs may act by partially inhibiting the N-terminal Met-Cys cleavage and thereby partially stabilizing an otherwise short-lived repressor(s) of angiogenesis that bears a Cys-containing N-degron. If the repressor's half-life is normally short enough, even a small fraction of repressor molecules that retain Met-Cys and are, therefore, long-lived, would yield a strong increase in the repressor's steady-state level, thereby possibly accounting for the finding that even a partial inhibition of MetAP2 is sufficient to block proliferation of endothelial cells. Likewise, inhibition of the cysteine oxidase pathway and/or arginylation dependent pathway also is likely to block such proliferation.

REFERENCES

1. A. Bachmair, D. Finley, A. Varshavsky, Science 234, 179-186 (1986).
2. A. Varshavsky, Proc. Natl. Acad. Sci. USA 93, 12142-12149 (1996).
3. Y. T. Kwon, Z.-X. Xia, I. V. Davydov, S. H. Lecker, A. Varshavsky, Mol. Cell. Biol. 21, 8007-8021 (2001).
4. A. Hershko, A. Ciechanover, A. Varshavsky, Nature Med. 10, 1073-1081 (2000).
5. H. Rao, F. Uhlmann, K. Nasmyth, A. Varshavsky, Nature 410, 955-960 (2001).
6. G. C. Turner, F. Du, A. Varshavsky, Nature 405, 579-583 (2000 Jun. 1, 2000).
7. Y. T. Kwon et al., Mol. Cell. Biol. 20, 4135-4148 (2000 June, 2000).
8. I. V. Davydov, A. Varshavsky, J. Biol. Chem. 275, 22931-22941 (2000).
9. Y. T. Kwon, A. S. Kashina, A. Varshavsky, Mol. Cell. Biol. 19, 182-193 (1999 January, 1999).
10. C. Pickart, Annu. Rev. Biochem. 70, 503-533 (2001).
11. D. K. Gonda et al., J. Biol. Chem. 264, 16700-16712 (1989).
12. M. Jaber et al., Proc. Natl. Acad. Sci. USA 93, 12794-12979 (1996).
13. D. Srivastava, Annu. Rev. Physiol. 63, 451-469 (2001).
14. T. L. Creazzo, E. G. Robert, L. Leatherbury, S. J. Conway, M. L. Kirby, Annu. Rev. Physiol. 60, 267-286 (1998).
15. T. Suzuki, A. Varshavsky, EMBO J. 18, 6017-6026 (1999 Nov. 1, 1999).
16. G. C. Turner, A. Varshavsky, Science 289, 2117-2120 (2000).
17. T. Tetaz, J. R. Morrison, J. Andreaou, N. H. Fidge, Biochem. Int. 22, 561-566 (1990).
18. T. Yagi, H. Kagamiyama, M. Nozaki, Biochem. Biophys. Res. Comm. 90, 447-452 (1979).
19. F. M. Ausubel et al., Eds., Current Protocols in Molecular Biology. (Wiley-Interscience, New York, 2000).
20. J. Li, C. M. Pickart, Biochemistry 34, 15829-15837 (1995).
21. H. Kaiji, G. D. Novelli, A. Kaiji, Biochim. Biophys. Acta 76, 474-479 (1963).
22. R. L. Soffer, in Transfer RNA: Biological Aspects. D. Söll, J. Abelson, P. R. Schimmel, Eds. (Cold Spring Harbor Laboratory Press, Cold Spring Harbor, N.Y., 1980) pp. 493-505.
23. S. Qusti et al., Cell Biol. Toxicol. 16, 243-255 (2000).
24. Y. M. Wang, N. A. Ingoglia, Neurochem. Res. 22, 1453-1459 (1997).
25. S. Hauf, I. C. Waizenegger, J.-M. Peters, Science 293, 1320-1323 (2001).
26. E. C. Griffith et al., Chem. Biol. 4, 461-471 (1997).
27. N. Sin et al., Proc. Natl. Acad. Sci. USA 94, 6099-7103 (1997).
28. R. K. Bruick, S. L. McKnight, Science 294, 1337-1340 (2001).
29. Y. T. Kwon et al., Proc. Natl. Acad. Sci. USA 95, 7898-7903 (1998).
30. K. Takao, K. Samejima, Biol. Pharm. Bull. 22, 1007-1009 (1999).
31. Q. Ma, Z. Chen, I. del Barco Barrantes, J. L. de la Pompa, D. J. Anderson, Neuron 20, 469-482 (1998).

Although the invention has been described with reference to the above examples, it will be understood that modifications and variations are encompassed within the spirit and scope of the invention. Accordingly, the invention is limited only by the following claims.

---

What is claimed is:

1. A method of screening for a modulator of N-terminal arginylation activity, comprising:
   a) contacting at least one potential modulator of N-terminal arginylation activity with a first cell that expresses a first reporter protein, wherein the first reporter protein has an N-terminal aspartic acid, glutamic acid or cysteine residue and a half-life that is affected by arginylation of the N-terminal residue, wherein the N-terminal arginylation activity is mediated by ATE-1 encoded Arg-tRNA-protein transferase;
   b) measuring the level of the reporter protein expressed by the first cell and the level of reporter protein expressed by a control cell not exposed to the at least one potential modulator;
   c) comparing the level of the reporter protein expressed by the first cell with the level of reporter protein expressed by the control cell, wherein a difference in levels is indicative of modulation of N-terminal arginylation activity, thereby screening for a modulator of N-terminal arginylation activity.

2. The method of claim 1, wherein the first cell and the control cell are cultured mammalian cells.

3. The method of claim 1, wherein the first cell and the control cell are yeast cells.

4. The method of claim 1, wherein the first cell and the control cell are bacterial cells.

5. The method of claim 1, wherein the reporter protein is a cleavable fusion protein comprising a reporter protein and a ubiquitin domain functionally linked to the reporter protein, wherein the reporter protein comprises an N-terminal aspartic acid, glutamic acid or cysteine.

6. The method of claim 1, wherein the reporter protein is a selectable marker protein, and the measuring comprises measuring survival of the cell under selection conditions.

7. The method of claim 6, wherein the selectable marker protein is an antibiotic resistance protein and the selection conditions comprise contacting the cell with the antibiotic.

8. The method of claim 1, wherein the measuring comprises fluorescence detection of the reporter protein.

9. The method of claim 1, wherein the reporter protein is a fluorescent protein.

10. The method of claim 9, wherein the fluorescent protein is Aequorea green fluorescent protein.

11. The method of claim 1, wherein the reporter protein is a light-generating protein.

12. The method of claim 11, wherein the light-generating protein is luciferase.

13. The method of claim 1, wherein the reporter protein is an enzyme.

14. The method of claim 13, wherein the enzyme is beta-galactosidase.

15. The method of claim 1, wherein expression of the reporter protein is inducible.

16. The method of claim 1, wherein the reporter protein has a half-life in the cell of less than about an hour in the absence of a modulator.

17. The method of claim 1, wherein the reporter protein has a half-life in the cell of less than about 10 minutes in the absence of a modulator.

18. The method of claim 1, wherein an increase in the steady-state level of the reporter fusion protein that has N-terminal aspartic acid identified an inhibitor of the arginyl transferase activity encoded by ATE-1.

19. The method of claim 1, further comprising:
   d) contacting the at least one potential modulator of N-terminal arginylation activity with a second cell that expresses a second reporter protein, having an N-terminal arginine residue, wherein the half-life of the second reporter protein is not affected by N-terminal arginylation;
   e) measuring the level of the reporter protein expressed by the second cell;
   f) comparing the level of the reporter protein expressed by the second cell with the level of reporter protein expressed by the first cell, wherein a difference in levels indicates modulation of N-terminal arginylation activity.

20. The method of claim 19, wherein the second cell is the same cell as the first cell in step a) expressing both the first reporter protein and the second reporter protein.

21. The method of claim 1, further comprising repeating steps b) and c) with a plurality of identical cells that each express the reporter protein with an N-terminal aspartic acid, glutamic acid or cysteine residue.

22. The method of claim 21, wherein each of the plurality of cells is contacted with a different potential modulator.

23. The method of claim 21, wherein each of the plurality of cells is contacted with a different concentration of the same potential modulator.

24. The method of claim 21, wherein each of the cells is in a different well of a microtiter plate.

* * * * *

UNITED STATES PATENT AND TRADEMARK OFFICE
CERTIFICATE OF CORRECTION

PATENT NO.      : 7,588,901 B2                          Page 1 of 1
APPLICATION NO. : 11/473568
DATED           : September 15, 2009
INVENTOR(S)     : Kwon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 101 days.

Signed and Sealed this

Twenty-first Day of September, 2010

David J. Kappos
*Director of the United States Patent and Trademark Office*

SEQUENCE LISTING

<160> NUMBER OF SEQ ID NOS: 2

<210> SEQ ID NO 1

```
<211> LENGTH: 518
<212> TYPE: PRT
<213> ORGANISM: Homo sapiens

<400> SEQUENCE: 1

Met Ala Phe Trp Ala Gly Gly Ser Pro Ser Val Val Asp Tyr Phe Pro
1               5                   10                  15

Ser Glu Asp Phe Tyr Arg Cys Gly Tyr Cys Lys Asn Glu Ser Gly Ser
                20                  25                  30

Arg Ser Asn Gly Met Trp Ala His Ser Met Thr Val Gln Asp Tyr Gln
            35                  40                  45

Asp Leu Ile Asp Arg Gly Trp Arg Arg Ser Gly Lys Tyr Val Tyr Lys
        50                  55                  60

Pro Val Met Asn Gln Thr Cys Cys Pro Gln Tyr Thr Ile Arg Cys Arg
65                  70                  75                  80

Pro Leu Gln Phe Gln Pro Ser Lys Ser His Lys Val Leu Lys Lys
                85                  90                  95

Met Leu Lys Phe Leu Ala Lys Gly Glu Val Pro Lys Gly Ser Cys Glu
                100                 105                 110

Asp Glu Pro Met Asp Ser Thr Met Asp Ala Val Ala Gly Asp Phe
            115                 120                 125

Ala Leu Ile Asn Lys Leu Asp Ile Gln Cys Asp Leu Lys Thr Leu Ser
        130                 135                 140

Asp Asp Ile Lys Glu Ser Leu Glu Ser Glu Gly Lys Asn Ser Lys Lys
145                 150                 155                 160

Glu Glu Pro Gln Glu Leu Leu Gln Ser Gln Asp Phe Val Gly Glu Lys
                165                 170                 175

Leu Gly Ser Gly Glu Pro Ser His Ser Val Lys Val His Thr Val Pro
            180                 185                 190

Lys Pro Gly Lys Gly Ala Asp Leu Ser Lys Pro Pro Cys Arg Lys Ala
        195                 200                 205

Lys Glu Ile Arg Lys Glu Arg Lys Leu Lys Leu Met Gln Gln Asn
210                 215                 220

Pro Ala Gly Glu Leu Glu Gly Phe Gln Ala Gln Gly His Pro Pro Ser
225                 230                 235                 240

Leu Phe Pro Pro Lys Ala Lys Ser Asn Gln Pro Lys Ser Leu Glu Asp
                245                 250                 255

Leu Ile Phe Glu Ser Leu Pro Glu Asn Ala Ser His Lys Leu Glu Val
            260                 265                 270

Arg Val Val Arg Ser Ser Pro Ser Ser Gln Phe Lys Ala Thr Leu
        275                 280                 285

Leu Glu Ser Tyr Gln Val Tyr Lys Arg Tyr Gln Met Val Ile His Lys
290                 295                 300

Asn Pro Pro Asp Thr Pro Thr Glu Ser Gln Phe Thr Arg Phe Leu Cys
305                 310                 315                 320

Ser Ser Pro Leu Glu Ala Glu Thr Pro Pro Asn Gly Pro Asp Cys Gly
                325                 330                 335

Tyr Gly Ser Phe His Gln Gln Tyr Trp Leu Asp Gly Lys Ile Ile Ala
            340                 345                 350

Val Gly Val Ile Asp Ile Leu Pro Asn Cys Val Ser Ser Val Tyr Leu
        355                 360                 365

Tyr Tyr Asp Pro Asp Tyr Ser Phe Leu Ser Leu Gly Val Tyr Ser Ala
370                 375                 380

Leu Arg Glu Ile Ala Phe Thr Arg Gln Leu His Glu Lys Thr Ser Gln
385                 390                 395                 400
```

```
Leu Ser Tyr Tyr Tyr Met Gly Phe Tyr Ile His Ser Cys Pro Lys Met
                405                 410                 415
Lys Tyr Lys Gly Gln Tyr Arg Pro Ser Asp Leu Leu Cys Pro Glu Thr
            420                 425                 430
Tyr Val Trp Val Pro Ile Glu Gln Cys Leu Pro Ser Leu Glu Asn Ser
        435                 440                 445
Lys Tyr Cys Arg Phe Asn Gln Asp Pro Glu Ala Val Asp Glu Asp Arg
    450                 455                 460
Ser Thr Glu Pro Asp Arg Leu Gln Val Phe His Lys Arg Ala Ile Met
465                 470                 475                 480
Pro Tyr Gly Val Tyr Lys Lys Gln Lys Asp Pro Ser Glu Glu Ala
                485                 490                 495
Ala Val Leu Gln Tyr Ala Ser Leu Val Gly Gln Lys Cys Ser Glu Arg
                500                 505                 510
Met Leu Leu Phe Arg Asn
        515

<210> SEQ ID NO 2
<211> LENGTH: 1557
<212> TYPE: DNA
<213> ORGANISM: Homo sapiens

<400> SEQUENCE: 2
atggctttct gggcgggggg ttcgcccagc gtcgtggact atttccctag cgaggacttc      60
taccgctgcg gctactgcaa gaacgagtcg ggcagccgct ccaatggcat gtgggcacat     120
tccatgacag tacaggatta tcaggatctc atagaccgag gatggcgaag aagtggaaaa     180
tatgtgtaca aacctgtcat gaatcaaaca tgttgtcctc agtacacaat aaggtgccga     240
cctttacaat ttcagccttc aaaatctcac aagaaggttt tgaaaaaaat gttgaaattt     300
ctagctaaag gggaggttcc caaaggaagt tgtgaggatg agcccatgga ttccacaatg     360
gatgatgctg ttgcgggtga cttttgcatt gataaataaac tggatataca gtgtgatctt     420
aaaacactca gtgatgacat caagagagt ttagagagtg aaggaaaaaa ttcaaagaaa     480
gaagaacctc aggaattact tcagtcacaa gatttcgtag agagaagtt gggctctggt     540 gaaccgtcac attcagttaa agttcacaca gttcctaagc caggcaaagg ggctgatttg     600
agtaagcctc catgtcgaaa agcaaaggaa tccggaaag aaaggaaaag gttaaaacta     660
atgcagcaga acccagctgg agaacttgag ggtttccagg ctcaaggtca cccaccatct     720
ttgtttccac caaaggctaa atccaaccag ccaaaatcac tcgaagattt aattttttgag     780 tctttaccag agaatgcatc acacaagtta gaggtgaggg tggtgagatc atctccacca     840
agttcgcagt tcaaagccac acttctggag tcttaccagg tctataaacg ttaccagatg     900
gttattcaca agaaccccac ctgatacgcca accgaaagcc agttcacaag attcctttgc     960
agttcaccct tggaggcaga gactcccct aatgggccag attgtggcta tggctccttt    1020
caccagcagt actggcttga cggaaagatc attgctgtgg gggtgattga catcctccca    1080
aactgtgtat catctgtgta tttgtactac gatcctgatt attcgttttt gtctttgggc    1140
gtctactctg cactacgaga aattgctttt actaggcagc ttcatgagaa aacttctcaa    1200
ctcagctatt attatatggg tttctacatt cattcatgtc ccaagatgaa atataagggt    1260
cagtatagac cttctgattt gctgtgccct gagacatatg tttgggtacc cattgagcaa    1320
tgcctgcctt cacttgaaaa ctccaagtac tgccgtttca accaggaccc agaagcagtg    1380
gatgaggatc gcagtacgga acctgaccga ttgcaggtgt tcacaagag agccatcatg    1440
```

```
ccttacggtg tttataagaa acagcagaaa gacccaagtg aggaggctgc tgttctgcag    1500
tacgccagcc tggtggggca gaagtgctcc gagcggatgc tgctgttcag aaactga      1557
```